(12) United States Patent
Ramanujam et al.

(10) Patent No.: US 7,952,704 B2
(45) Date of Patent: May 31, 2011

(54) OPTICAL ASSAY SYSTEM FOR INTRAOPERATIVE ASSESSMENT OF TUMOR MARGINS

(75) Inventors: Nirmala Ramanujam, Chapel Hill, NC (US); Lee G. Wilke, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 12/830,078

(22) Filed: Jul. 2, 2010

(65) Prior Publication Data

US 2010/0301229 A1  Dec. 2, 2010

Related U.S. Application Data

(62) Division of application No. 11/729,967, filed on Mar. 29, 2007, now Pat. No. 7,751,039.

(60) Provisional application No. 60/787,462, filed on Mar. 30, 2006.

(51) Int. Cl.
*G01N 21/01* (2006.01)
(52) U.S. Cl. ............................ 356/244; 356/246; 422/67
(58) Field of Classification Search .................. 356/244, 356/246, 36–39, 445, 344; 250/458.1, 492.1; 422/67, 82, 86; 436/172; 382/128, 132, 382/140; 600/310, 316
See application file for complete search history.

(56) References Cited

U.S. PATENT DOCUMENTS

| | | | |
|---|---|---|---|
| 4,034,884 A | 7/1977 | White | |
| 4,580,895 A | 4/1986 | Patel | |
| 5,203,328 A | 4/1993 | Samuels et al. | |
| 5,439,578 A | 8/1995 | Dovichi et al. | |
| 5,452,723 A | 9/1995 | Wu et al. | |
| 5,529,391 A | 6/1996 | Kindman et al. | |
| 5,582,168 A | 12/1996 | Samuels et al. | |
| 5,813,403 A | 9/1998 | Soller et al. | |
| 5,924,981 A | 7/1999 | Rothfritz et al. | |
| 5,976,892 A | 11/1999 | Bisconte | |
| 6,055,451 A | 4/2000 | Bambot et al. | |
| 6,219,566 B1 | 4/2001 | Weersink et al. | |
| 6,411,373 B1 | 6/2002 | Garside et al. | |
| 6,549,284 B1 | 4/2003 | Boas et al. | |
| 6,564,088 B1 | 5/2003 | Soller et al. | |
| 6,574,490 B2 * | 6/2003 | Abbink et al. | 600/316 |
| 6,577,391 B1 | 6/2003 | Faupel et al. | |
| 6,590,651 B1 | 7/2003 | Bambot et al. | |
| 6,662,030 B2 | 12/2003 | Khalil et al. | |

(Continued)

OTHER PUBLICATIONS

Non-Final Official Action for U.S. Appl. No. 12/036,717 (Aug. 17, 2010).

(Continued)

*Primary Examiner* — Sang Nguyen
(74) *Attorney, Agent, or Firm* — Jenkins, Wilson, Taylor & Hunt, P.A.

(57) ABSTRACT

The subject matter described herein includes an optical assay system for intraoperative assessment of tumor margins. According to one aspect, the subject matter described herein includes a biological sample containment and illumination apparatus for holding a biological sample for illumination by a plurality of electromagnetic radiation probes. The biological sample containment and illumination apparatus includes a plurality of frame members positioned with respect to each other to form an interior space for receiving a biological sample. At least one of the plurality of frame members includes a plurality of probe receiving locations for receiving a plurality of electromagnetic radiation probes. The probe receiving locations position the probes with respect to the biological sample to allow illumination of plural locations of the biological sample by the probes.

40 Claims, 8 Drawing Sheets

U.S. PATENT DOCUMENTS

| | | |
|---|---|---|
| 6,678,541 B1 | 1/2004 | Durkin et al. |
| 6,813,515 B2 | 11/2004 | Hashimshony |
| 6,850,656 B1 | 2/2005 | Bevilacqua et al. |
| 6,870,620 B2 | 3/2005 | Faupel et al. |
| 6,912,412 B2 | 6/2005 | Georgakoudi et al. |
| 6,965,345 B2 | 11/2005 | Bae et al. |
| 6,975,899 B2 | 12/2005 | Faupel et al. |
| 7,006,220 B2 | 2/2006 | Bambot et al. |
| 7,030,988 B2 | 4/2006 | Kubo et al. |
| 7,062,333 B2 | 6/2006 | Mizutani |
| 7,064,837 B2 | 6/2006 | Mori et al. |
| 7,082,325 B2 | 7/2006 | Hashimshony et al. |
| 7,113,624 B2 | 9/2006 | Curry |
| 7,129,454 B2 | 10/2006 | O'Connell et al. |
| 7,145,645 B2 | 12/2006 | Blumenfeld et al. |
| 7,184,824 B2 | 2/2007 | Hashimshony |
| 7,202,947 B2 | 4/2007 | Liu et al. |
| 7,236,815 B2 | 6/2007 | Richards-Kortum et al. |
| 7,382,258 B2 | 6/2008 | Oldham et al. |
| 7,403,812 B2 | 7/2008 | Rice et al. |
| 7,411,680 B2 | 8/2008 | Chang et al. |
| 7,570,988 B2 | 8/2009 | Ramanujam et al. |
| 7,751,039 B2 | 7/2010 | Ramanujam et al. |
| 7,818,154 B2 | 10/2010 | Palmer et al. |
| 7,835,786 B2 | 11/2010 | Palmer et al. |
| 2002/0055671 A1 | 5/2002 | Wu et al. |
| 2002/0084417 A1 | 7/2002 | Khalil et al. |
| 2002/0114734 A1 | 8/2002 | Pantoliano et al. |
| 2004/0073120 A1* | 4/2004 | Motz et al. ............ 600/478 |
| 2005/0239197 A1 | 10/2005 | Katerkamp et al. |
| 2006/0247532 A1 | 11/2006 | Ramanujam et al. |
| 2007/0019199 A1 | 1/2007 | Palmer et al. |
| 2007/0232932 A1 | 10/2007 | Palmer et al. |
| 2007/0282575 A1 | 12/2007 | Gossage |
| 2008/0056957 A1 | 3/2008 | Hayman |
| 2008/0270091 A1 | 10/2008 | Ramanujam et al. |
| 2009/0015826 A1 | 1/2009 | Ramanujam et al. |

OTHER PUBLICATIONS

Notice of Allowance and Fee(s) Due for U.S. Appl. No. 11/729,967 (Feb. 19, 2010).
Notice of Allowance and Fee(s) Due for U.S. Appl. No. 11/729,967 (Oct. 22, 2009).
Interview Summary for U.S. Appl. No. 11/729,967 (Sep. 24, 2009).
Official Action for U.S. Appl. No. 11/729,967 (May 28, 2009).
Restriction and/or Election Requirement for U.S. Appl. No. 11/729,967 (Apr. 17, 2009).
Communication pursuant to Article 94(3) EPC for European Application No. 07 753 265.3 (Mar. 18, 2011).
Extended European Search Report for European Application No. 07754152.2 (Feb. 15, 2011).

* cited by examiner

OPTICAL ASSAY SYSTEM FOR INTRAOPERATIVE ASSESSMENT OF TUMOR MARGINS

CROSS REFERENCE TO RELATED APPLICATIONS

This application is a divisional of U.S. patent application Ser. No. 11/729,967, filed Mar. 29, 2007 now U.S. Pat. No. 7,751,039, which claims the benefit of U.S. Provisional Patent Application Ser. No. 60/787,462, filed Mar. 30, 2006, the disclosures of which are incorporated herein by reference in their entireties.

GOVERNMENT INTEREST

This presently disclosed subject matter was made with U.S. Government support under Grant No. R01-CA100559-01A1 awarded by the United States National Institutes of Health/National Cancer Institute. Thus, the U.S. Government has certain rights in the presently disclosed subject matter.

TECHNICAL FIELD

The subject matter described herein relates to methods, compositions, and systems for detecting electromagnetic radiation reflected from or emitted by a biological sample. More particularly, the subject matter described herein relates to an apparatus for holding a biological sample for illumination by a plurality of electromagnetic radiation probes, and methods and systems for using the apparatus to determine an indication of a physical property of the biological sample.

BACKGROUND

Cancer is a significant cause of illness-related deaths in the United States. A common therapy for cancer is surgical resection of the tumor, followed by radiation, chemotherapy, or both radiation and chemotherapy. The goal of these therapies is to remove the observable tumor itself and as much additional surrounding tissue as possible in order to decrease the likelihood that pre-neoplastic or neoplastic cells that appear morphologically normal remain in the subject that can later form the basis of a recurrence or metastasis.

In many cases, however, there is a desire to limit the removal of surrounding tissue to the greatest extent possible in order to maintain the appearance and/or function of the tissue from which the tumor was resected. In order to balance the desire to remove potentially neoplastic tissue while preserving normal tissue, the surgeon will often be supported by a pathologist, who during or subsequent to the resection procedure examines the excised tissue. The pathologist's examination is designed to determine if a sufficient boundary of normal tissue surrounding the tumor has been removed to suggest that any potentially neoplastic cells have been resected. This examination of the tumor margin also can be used to determine whether further surgical intervention is necessary.

One situation where the interplay between the desire to completely remove a tumor and yet to minimize the removal of normal tissue is prominent is in breast cancer. It is estimated that about 125,000 women diagnosed with early stage breast cancer receive breast conserving surgery (BCS) each year. BCS involves removal of the cancer with a surrounding margin of normal breast tissue. An important predictor of local recurrence after BCT is pathologic margin status. Reported rates of re-excision surgery as a result of close or positive surgical margins are high (10-40%). Intraoperative frozen section and touch prep cytology have been developed to assess surgical margins and guide additional resection at the time of the initial operation. However, these techniques have not been widely adopted because of the need for specially trained personnel (pathologist), prolonged surgical time required for specimen processing (20-40 minutes), significant technical challenges, and limited coverage of the tumor margins (less than 1% of the margins are examined).

At least in part because of these limitations, re-excision of the tumor site is frequently required. To decrease the need for re-excision, several intra operative techniques have been developed to assess surgical margins and guide additional resection at the time of the initial operation. These methods include intra operative frozen section and touch prep cytology. Among the drawbacks of these techniques are the need for specially trained personnel (pathologist), prolonged surgical time required for specimen processing (20-40 minutes), technical problems related to freezing and cutting tissue with high fat content, and limited surveillance of the tumor margins. Moreover, pathological margin assessment relies on visual inspection of the specimen and is unreliable for grossly occult lesions such as DCIS or invasive lobular carcinoma. Thus, these methods have not been widely adopted for intra operative assessment of margins.

What are needed, then, are robust, reliable, and rapid strategies for assessing tumor margins. To address this need, at least in part, the subject matter described herein provides methods and systems for imaging biological samples.

SUMMARY

The subject matter described herein includes an optical assay system for intraoperative assessment of tumor margins. According to one aspect, the subject matter described herein includes a biological sample containment and illumination apparatus for holding a biological sample for illumination by a plurality of electromagnetic radiation probes. The biological sample containment and illumination apparatus includes a plurality of frame members positioned with respect to each other to form an interior space for receiving a biological sample. At least one of the plurality of frame members includes a plurality of probe receiving locations for receiving a plurality of electromagnetic radiation probes. The probe receiving locations position the probes with respect to the biological sample to allow illumination of plural locations of the biological sample by the probes.

The subject matter described herein also includes a method for testing a biological sample. The method includes placing a biological sample in an interior space defined by a biological sample containment and illumination apparatus having a plurality of frame members, at least one of which includes a plurality of probe receiving locations for receiving a plurality of electromagnetic radiation probes and for positioning the probes with respect to the sample to allow illumination of plural locations of the sample by the probes. The biological sample is illuminated through the probe receiving locations using the probes. Electromagnetic radiation reemitted from the biological sample is detected.

The subject matter described herein further includes a system for imaging a sample. The system includes a biological sample containment and illumination apparatus for holding a biological sample for illumination by a plurality of electromagnetic radiation probes. The biological sample containment and illumination apparatus includes a plurality of frame members positioned with respect to each other to form an interior space for receiving a biological sample. At least one of the plurality of frame members includes a plurality of probe receiving locations for receiving a plurality of electromagnetic radiation probes and for positioning the probes with respect to the biological sample to allow illumination of plural locations of the biological sample by the probes. A plurality of electromagnetic radiation probes is provided for illuminating the plural locations of the biological sample via the probe receiving locations with electromagnetic radiation generated by an electromagnetic radiation source and for detecting electromagnetic radiation reflected or emitted by the biological sample via the probe receiving locations. A processor is coupled to probes for receiving reemitted electromagnetic radiation and for determining an indication of a physical property of the biological sample.

As used herein, the phrase "biological sample" includes any sample that includes biological tissue. In some embodiments, a biological sample comprises a tumor biopsy, which is in some embodiments a breast tumor biopsy or a portion of a breast tumor that has been resected from a subject.

As used herein, the phrase "an indication of a physical property of the biological sample" refers to any physical property of a biological sample, including an assessment that is predictive of an area in the biological sample that has been imaged comprising all normal cells, all pre-neoplastic and/or neoplastic cells, or a combination thereof. In one implementation, the indication of the physical property may include an indication of the concentration of one or more absorbers or fluorophores or scatterer (cell nuclei) size in the biological sample.

BRIEF DESCRIPTION OF THE DRAWINGS

Preferred embodiments of the subject matter described herein will now be explained with reference to the accompanying drawings, of which.

DETAILED DESCRIPTION

All references cited herein are incorporated herein by reference in their entireties to the extent that they supplement, explain, provide a background for, or teach methodology, techniques, and/or compositions employed herein.

Reference will now be made in detail to exemplary embodiments of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Figure 1:
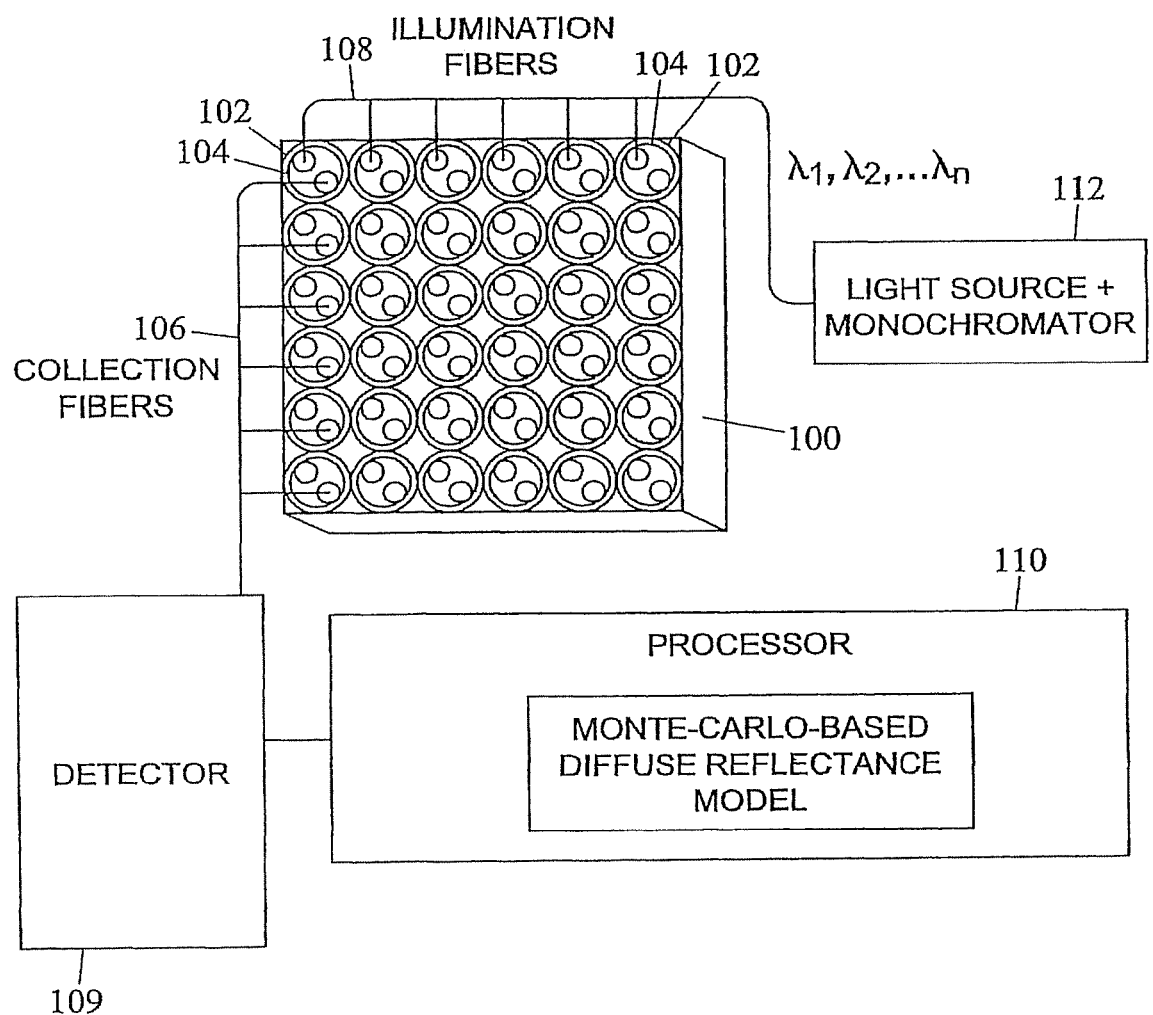
FIG. 1 is a block diagram of a system for imaging a biological sample according to an embodiment of the subject matter described herein.

The subject matter disclosed herein includes a biological sample containment and illumination apparatus and methods and systems for using the biological containment and illumination apparatus to an indication of a physical property of the biological sample. FIG. 1 is a block diagram illustrating exemplary components of a system for imaging a sample. Referring to FIG. 1, the system includes a biological sample containment and illumination apparatus 100 for holding a biological sample. Biological sample containment and illumination apparatus 100 may include a plurality of frame members positioned with respect to each other to form an interior space for receiving a biological sample. In one exemplary implementation, at least one of the plurality of frame members of biological containment and illumination apparatus 100 may be translatable with respect to another frame member such that the volume of interior space can be altered in at least one direction. In an alternate implementation containment and illumination apparatus 100, at least two of the plurality of frame members are translatable in order to alter the volume of the interior space in at least two directions.

Figure 2:
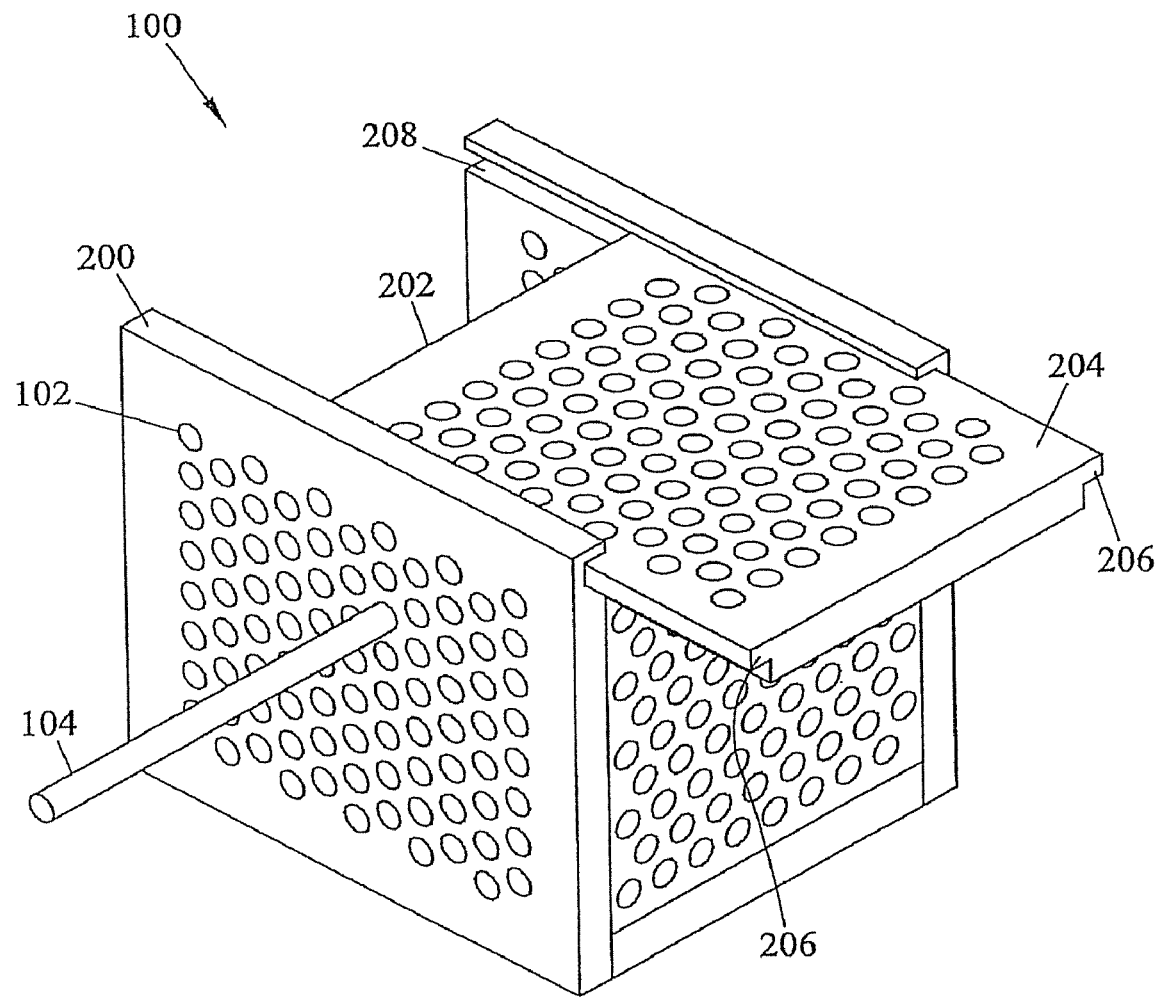
FIG. 2 is a perspective view of an exemplary biological sample containment and illumination apparatus according to an embodiment of the subject matter described herein showing a representative placement of an electromagnetic radiation probe.
Figure 3:
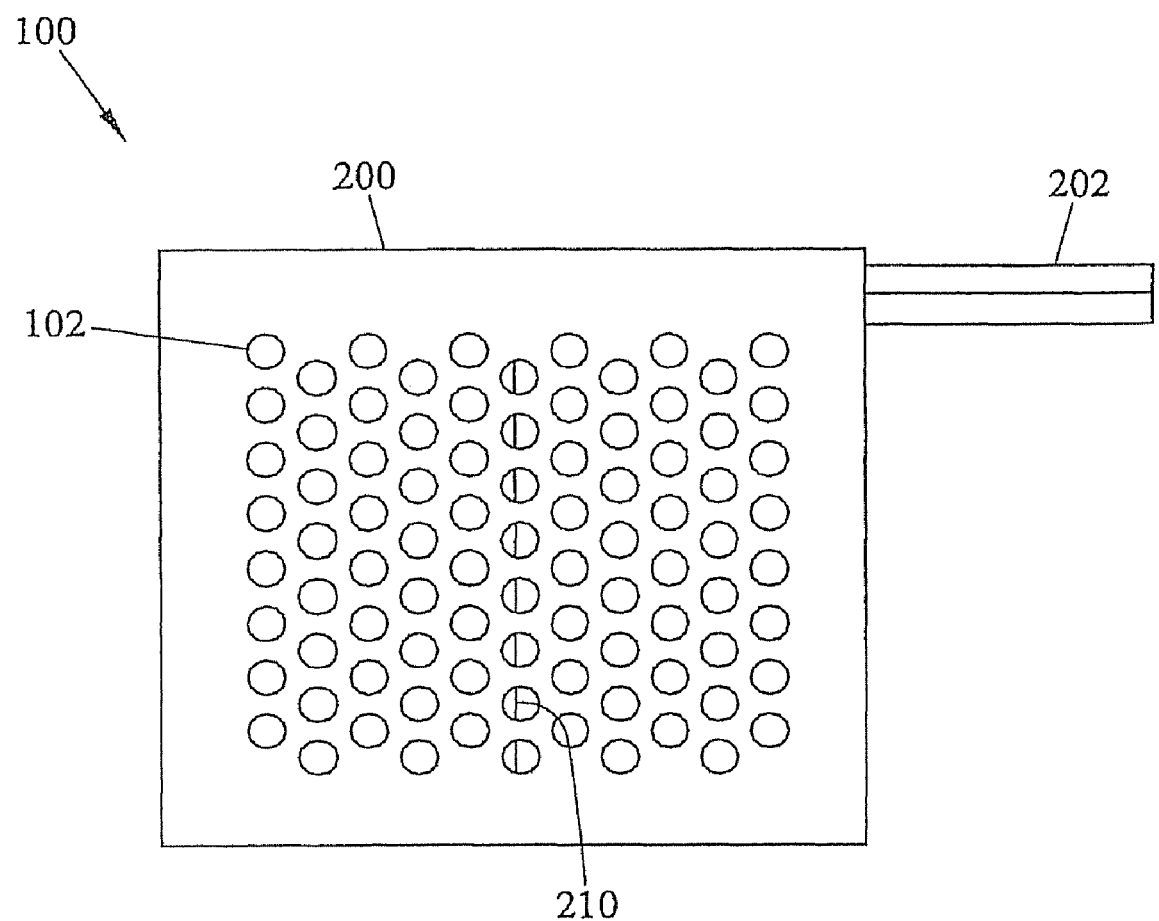
FIG. 3 is a side view of the biological sample containment and illumination apparatus of FIG. 2 showing decreasing of its interior volume according to an embodiment of the subject matter described herein.
Figure 4:
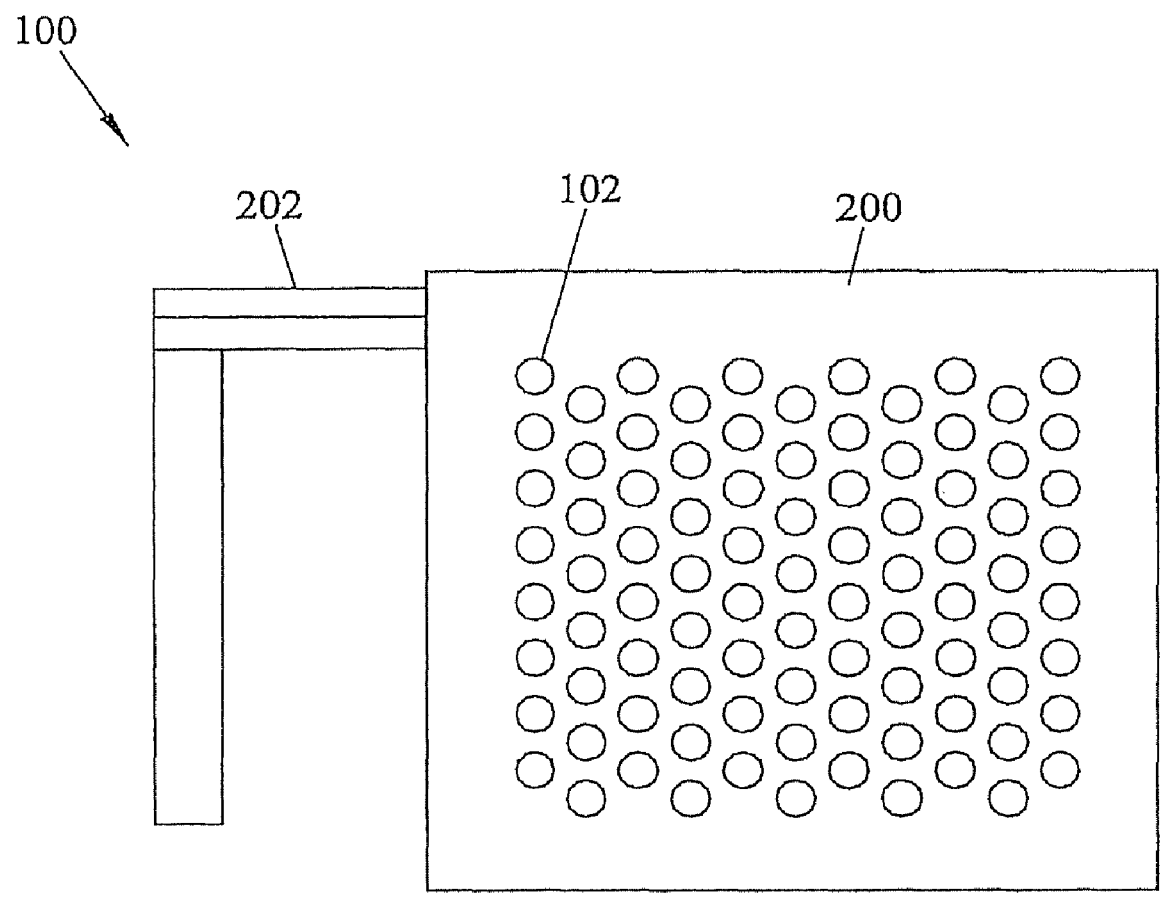
FIG. 4 is a reverse side view of the exemplary biological sample containment and illumination apparatus of FIG. 2 showing increasing of its interior volume according to an embodiment of the subject matter described herein.

In one implementation, biological sample containment and illumination apparatus 100 comprises a parallelepiped structure with two frame members that are moveable with respect to each other to vary the interior volume. FIGS. 2-5 illustrate different views of an exemplary biological sample containment and illumination apparatus according to an embodiment of the subject matter described herein. Referring to FIG. 2, biological sample illumination and containment apparatus 100 includes a first frame member 200 and a second frame member 202. Frame member 200 is translatable with respect to frame member 202 to vary the interior volume of biological sample containment and illumination apparatus 202. More particularly, a frame member 202 includes a first side 204 having extensions 206 that slide in grooves 208 of frame member 200. Frame member 202 also includes a second side 210 illustrated in FIG. 3 that extends orthogonally from first side 204. In FIG. 3, frame member 202 is moved with regard to frame member 200 to decrease the interior volume of biological sample containment and illumination apparatus 100. In FIG. 4, frame member 202 is moved outwardly with regard to frame member 200 to increase the volume defined by frame members 200 and 202 for holding a biological sample.

Figure 5:
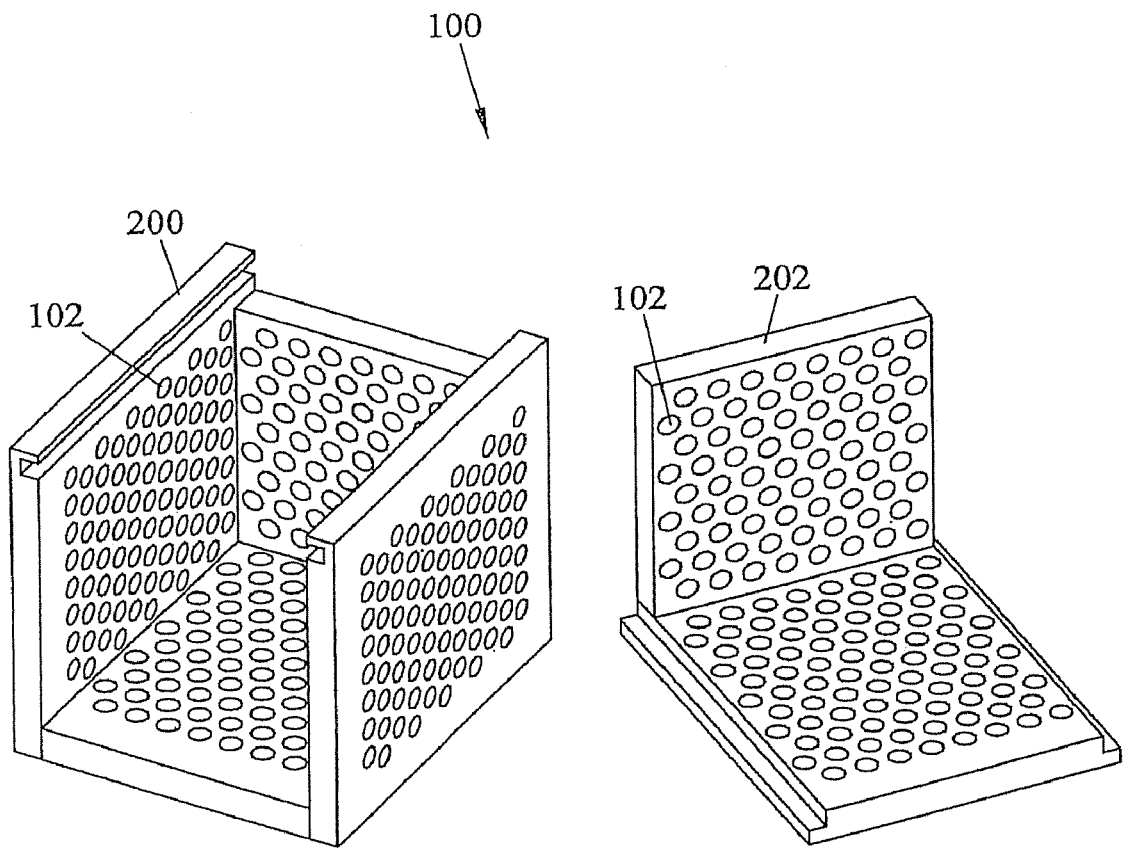
FIG. 5 is an exploded view of the biological sample containment and illumination apparatus of FIG. 2 according to an embodiment of the subject matter described herein.

In one exemplary implementation, frame members 200 and 202 are separable from each other to facilitate cleaning and placement of biological samples. FIG. 5 is an exploded view of frame members 200 and 202 illustrating their separability. As illustrated in FIG. 5, each side of frame member 200 as well as each side of frame member 202 includes plural probe receiving locations. Providing plural probe receiving locations allows for testing of a biological sample at plural locations on the sample without moving the biological sample. In one implementation, plural probes may be placed in plural probe receiving locations 102 to simultaneously or serially illuminate a biological sample. Returning to FIG. 2, a single probe 104 is shown as being positioned in one of probe receiving locations 102. However, it is understood that plural probes 104 may be simultaneously placed in plural probe receiving locations 102 to increase the speed at which a biological sample can be tested.

The subject matter described herein is not limited to providing a biological sample containment and illumination apparatus where one frame member is translatable with regard to another frame member. In an alternate implementation, the frame members of biological sample containment and illumination apparatus may be fixed with respect to each other to define a fixed volume. In order to test biological samples of different volumes, biological sample containment and illumination apparatuses of different interior volumes may be provided.

Biological sample containment and illumination apparatus 100 may be made of any suitable material. In order to allow a user to view the biological sample when placed inside of apparatus 100, the material may be transparent or translucent. In one implementation, biological containment and illumination apparatus 100 may be made of an acrylic glass material, such as polymethyl methacrylate.

The translatable frame member or members of biological sample containment and illumination apparatus 100 can be employed to alter the volume of the interior space so that it approximates the volume of the biological sample. For example, the biological sample can be placed within the interior space and allowed to settle to an initial position by gravity. The position of one or more translatable frame members can then be changed such that at least a portion of each frame member is in contact with a portion of the biological sample. If desired, the shape of the biological sample can be forced to conform to the shape of the interior space by using the translatable frame members to apply a pressing force to the biological sample.

In FIG. 1, at least one of the plurality of frame members of biological sample containment and illumination apparatus 100 includes a plurality of receiving locations, generally designated 102, for receiving a plurality of electromagnetic radiation probes, generally designated 104, and for positioning the plurality of electromagnetic radiation probes 104 with respect to the biological sample to allow illumination of plural locations of the biological sample by the probes. In some embodiments, each of the plurality of receiving locations 102 is adapted to receive a fiber optic probe. In one implementation, each probe receiving location 102 comprises an aperture.

Each fiber optic probe 104 may include at least one illumination fiber 106 and at least one collection fiber 108. Some fibers may be both illumination and collection fibers. An exemplary structure for probe 104 will be described in detail below.

The apertures of biological containment and illumination apparatus 100 can be spaced from each other so as to avoid cross-talk between adjacent probes. In one exemplary implementation, each of the apertures has a diameter of about 3.7 mm and adjacent apertures have a 2 mm radial separation. In some embodiments, of biological containment and illumination apparatus 100, the fiber optic probes have a sensing depth of between about 1 and 2 mm.

Figure 6:
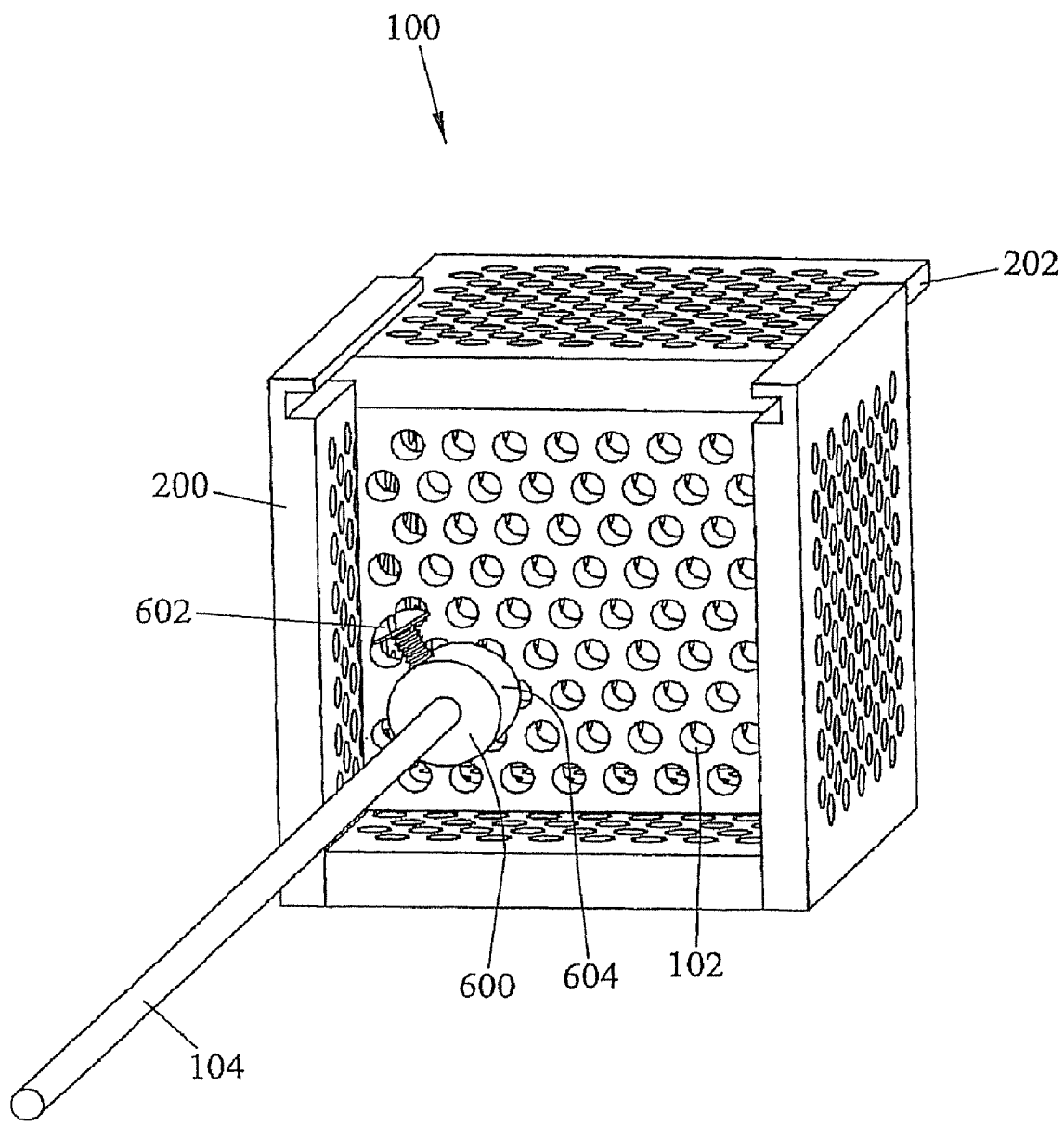
FIG. 6 is a view of the exemplary biological sample containment and illumination apparatus of FIG. 2 according to an embodiment of the subject matter described herein showing a representative placement of an electromagnetic radiation probe and the attachment of the electromagnetic radiation probe to an adapter.

In one implementation, biological sample containment and illumination apparatus 100 may include means for controlling advancement of each fiber optic probe in each aperture to position the fiber optic probe adjacent to the biological sample. In some embodiments, the means for controlling advancement of each fiber optic probe in each aperture includes a barrier located at an end of each aperture adjacent to the interior space to prevent the fiber optic probes from entering the interior space. Alternatively or in addition, the means for controlling advancement may include one or more adapters coupleable to one or more of the fiber optic probes to prevent the fiber optic probe from entering the interior space through the aperture. FIG. 6 illustrates an adapter 600 suitable for use with embodiments of the subject matter described herein. In FIG. 6, adapter 600 is coupled to fiber 104 and to one of apertures 102. A set screw 602 limits advancement of fiber 104 into adapter 600 and into the corresponding aperture 102. Adapter 600 may include a first portion (not shown) that is of a diameter to fit within one of apertures 102 and a second portion 604 that is larger than the diameter of apertures 102 to limit advancement of adapter 600 in its respective aperture. The reason for limiting advancement of probe 104 into apparatus 100 is to prevent probe 104 from deforming the biological sample being tested and thereby changing its optical properties. In some embodiments, the plurality of fiber optic probes are fixedly attached to each other such that the adapter that prevents the fiber optic probe to which it is attached from entering the interior space also prevents all of the plurality of fiber optic probes from entering the interior space.

Returning to FIG. 1, a detector 109 may detect the emitted or reflected light signals detected by collection fibers 106 and output electrical signals corresponding to the optical signals. In one implementation, detector 109 comprises a charge coupled device (CCD).

In order to account for the effects of probe geometry, and separate the effects of the absorbers, scatterers and fluorophores, the system illustrated in FIG. 1 includes a processor 110 that runs one or more simulations to generate a model of reflectance and then a model of fluorescence and then uses the model to generate an indication of a physical property of the biological sample. Processor 110 may receive as input simulation start parameters, an initial guess of the optical properties of the biological sample into the model of reflectance. In one implementation, these optical properties may include absorption coefficient, scattering coefficient, anisotropy factor, and refractive index. An iterative inversion scheme will be used to optimize the fits to retrieve the actual optical properties of the biological sample. These optical properties will used as inputs into the model of fluorescence to extract the intrinsic fluorescence. If the indication of intrinsic fluorescence to be determined is the concentration of one or more fluorophores, processor 110 may receive as input fluorophore characteristics, such as the extinction coefficient of the fluorophore at the excitation wavelength, the probability that a photon absorbed by a fluorophore will generate fluorescence, and the spectral probability distribution of the generated fluorescence at the emission wavelength. If these properties of the fluorophore are determined, then the concentration of the fluorophore in the biological sample can be determined. If these properties and not provided as input to processor 110, the indicator of intrinsic fluorescence may be an alternate measure of intrinsic fluorescence, such as the product of the quantum yield and the fluorophore concentration.

Monte Carlo modeling techniques can be used to design an optical probe that has a sensing depth of −2 mm within breast tissues. The Monte Carlo model allows simulation of light transport within a theoretical tissue-model for different optical probe geometries and outputs a number of relevant parameters including the total signal detected by the probe (which will give a measure of signal to noise) as well as the distribution of the light-photons within the tissue model (i.e., optical sensing depth). Representative Monte Carlo modeling techniques for this purpose are disclosed in co-pending U.S. patent application entitled "MONTE CARLO BASED MODEL OF FLUORESCENCE IN TURBID MEDIA AND METHODS AND SYSTEMS FOR USING SAME TO DETERMINE INTRINSIC FLUORESCENCE OF TURBID MEDIA" filed Mar. 16, 2007 and co-pending U.S. patent application Ser. No. 11/119,865 entitled "METHOD FOR EXTRACTION OF OPTICAL PROPERTIES FROM DIFFUSE REFLECTANCE SPECTRA" filed May 2, 2005, the disclosures of each of which is hereby incorporated by reference in its entirety.

Returning to FIG. 1, the system may include an electromagnetic radiation source 112 to illuminate a biological sample via probes 104. In one implementation, electromagnetic radiation source 112 may be a light source, such as a broadband light source and one or more color filters for illuminating a biological sample with different colors or wavelengths of light. In an alternate implementation, electromagnetic radiation source 112 may be a non-visible-light source, such as an infrared radiation source for illuminating a biological sample with infrared radiation. In yet another alternate implementation, electromagnetic radiation source 112 may include different narrowband light sources, such as LED light sources for illuminating a biological sample with different wavelengths.

Figure 7:
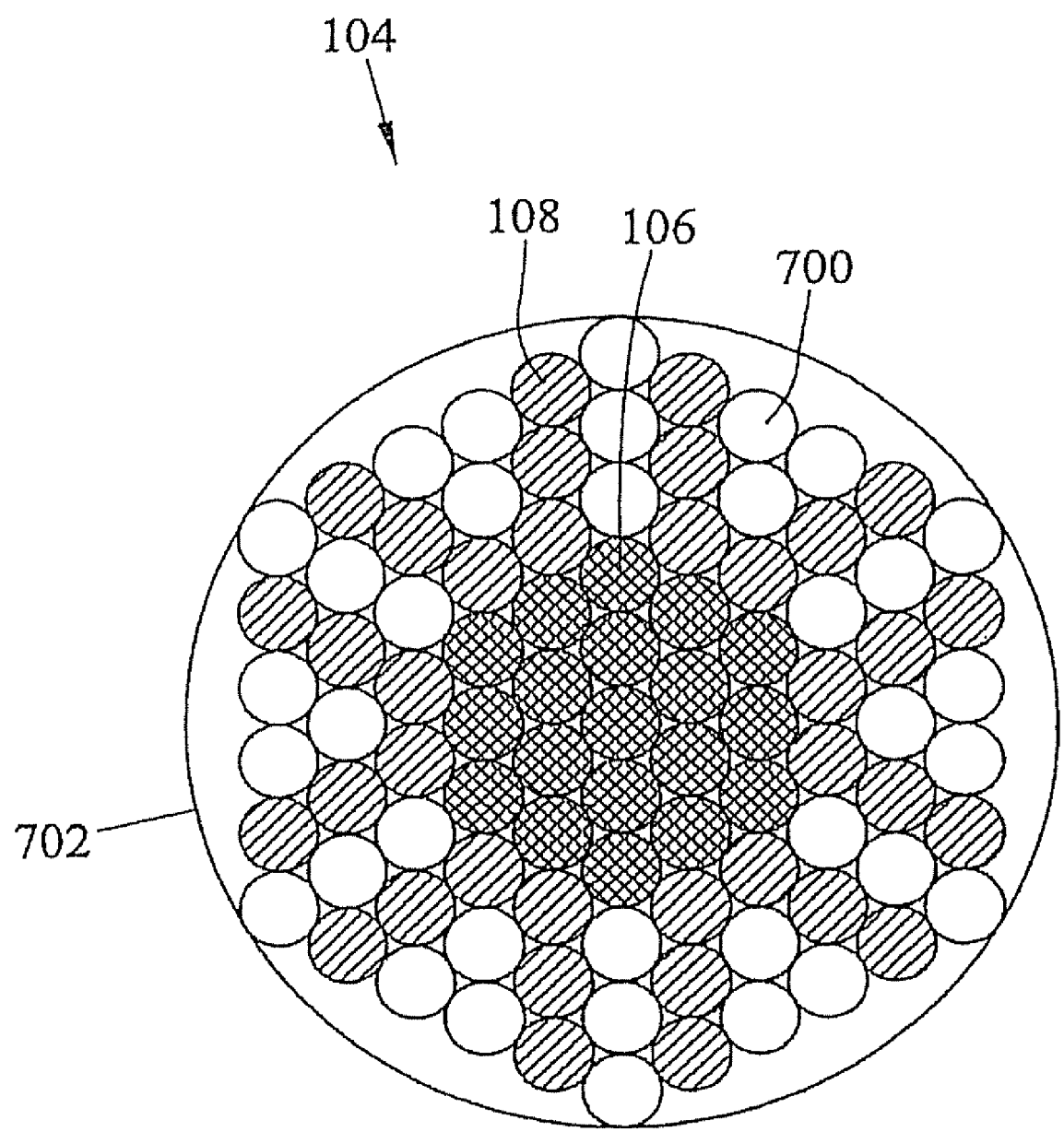
FIG. 7 is a cross-sectional view of a representative fiber optic probe showing a central core of illumination fibers (cross-hatched) surrounded by collection fibers (single-hatched) arranged in three concentric circles around the illumination fibers. Dead fibers (white) are included to form the geometry desired for the collection fibers.

As stated above, each probe 104 may include at least one illumination fiber 106 and at least one collection fiber 108. FIG. 7 illustrates an example of a probe geometry suitable for use with embodiments of the subject matter described herein. More particularly, in FIG. 7, a central core of illumination fibers 106 is shown by cross-hatching in each fiber. Collection fibers 108 concentrically surround illumination fibers 106. In the illustrated example, collection fibers 108 are shown by single hatching in each fiber. Fibers 700 are dead fibers that are not used for collection or illumination and are merely used to package the fibers in a bundle. In order to hold the fibers in a bundle, a sheath 702 surrounds fibers 106, 108, and 700. In one aspect of probe 104, the central core of illumination fibers 106 has a diameter of 1 mm, and each collection fiber 108 and fiber 700 has a diameter of 200 μm.

In operation, the tips of illumination fibers 106 are placed in contact with the tissue surface. Illumination fibers 106 deliver light from source 112 to the tissue surface. The light propagates through the tissue, and a fraction of the light propagating through the tissue volume exits the tissue surface as a diffuse reflectance signal. Collection fibers 108 collect a portion of the emitted light from the tissue surface and couples it to processor 110, which determines an indication of a physical property of the sample. The geometry of the illumination and collection fibers (separation between the fibers and their corresponding diameters) and the optical properties (absorption and scattering) of the tissue through which the light propagates, define the optical sensing depth (see Pfefer et al. (2003) *Optics Letters* 28:120-122; Zhu et al. (2003) *J Biomed Opt* 8:237-247; Zhu et al. (2006) *Lasers Surg Med* 38:714-724). See also Palmer et al. (2006) *Appl Opt* 45:1072-1078.

Figure 8:
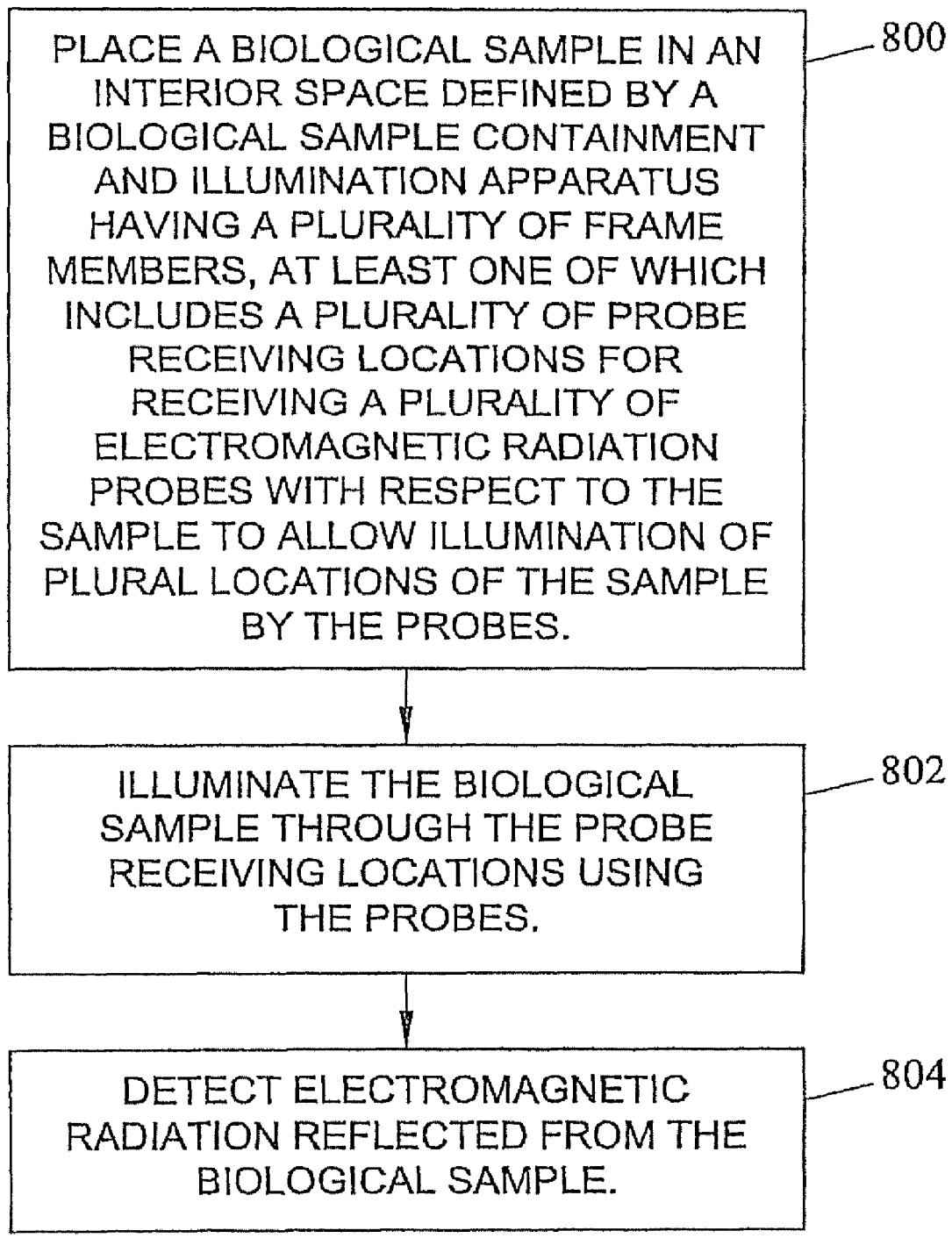
FIG. 8 is a flow chart of an exemplary process for testing a biological sample according to an embodiment of the subject matter described herein.

According to one aspect, the subject matter described herein includes a method for testing a biological sample. FIG. 8 is a flow chart of an exemplary method for testing a biological sample according to an embodiment of the subject matter described herein. Referring to FIG. 8, in step 800, the biological samples placed in the interior space defined by biological sample containment and illumination apparatus having a plurality of frame members. At least one of the frame members includes a plurality of probe receiving locations for receiving a plurality of electromagnetic radiation probes and for positioning the probes with respect to the sample to allow illumination of plural locations of the same by the probes. For example, a biological sample may be placed in biological sample containment and illumination apparatus 100 illustrated in FIG. 2. One or more probes 104 may be placed in probe receiving locations 102 to illuminate plural locations of the sample.

Returning to FIG. 8, in step 802, the biological sample is illuminated through the probe receiving locations using the probes. Referring to FIG. 1, a biological sample within containment apparatus 100 may be illuminated using one or more of probes 104 via light source 112.

Returning to FIG. 8, in step 804, electromagnetic radiation reflected from a biological sample is detected. Returning to FIG. 1, collection fibers 108 may detect electromagnetic radiation emitted from the biological sample and couple that radiation to processor 110 so that a physical property of the biological sample can be determined.

EXAMPLE

The following example illustrates an application of the subject matter described herein for intra-operative assessment of a breast tissue biopsy.

Immediately after surgical excision, a biological sample comprising a breast tissue biopsy is dabbed dry and placed in biological sample containment and illumination apparatus 100. Adjustments are made by translating one or more frame members until the tissue conforms to the shape of biological sample containment and illumination apparatus 100 and all 6 faces of the biological containment and illumination apparatus 100 are flush with the biological sample. One or more electromagnetic radiation probes is inserted into an aperture in one of the frame members of biological sample containment and illumination apparatus 100 until the tip of the electromagnetic radiation probe is flush with the inner surface of the biological containment and illumination apparatus (e.g., in contact with the surface of the biological sample) and an optical measurement is made. Specifically, a diffuse reflectance spectrum over a wavelength range of 400-650 nm is recorded. This measurement takes less than a second to complete. This procedure is repeated for all holes on the 6 faces of biological sample containment and illumination apparatus. Alternatively, an array of electromagnetic radiation probes is employed and diffuse reflectance spectrum over a wavelength range of 400-650 nm is recorded either simultaneously or sequentially for each of the electromagnetic radiation probes in the array. Depending on the number of electromagnetic radiation probes in the array and the number of apertures in the frame member, the array is repositioned and the readings taken for the new positions as necessary. The total measurement takes no more than 30 minutes. It has been shown previously that the optical properties of freshly excised tissue retains relatively unchanged during this period (see Palmer et al. (2002) *Lasers Surgery Med* 3:191-200).

After each measurements is completed, several sites on each face of the biological containment and illumination apparatus are labeled with colored ink such that these sites can be evaluated by a pathologist for positive or negative margins. The number of sites that are marked with ink per specimen is coordinated with a pathologist. Note that because only a fraction of the margins would be expected to be positive, the majority of the margins evaluated are negative for disease. To increase the representation of disease in the collected spectral data set, each specimen is be cut in half after the margins have been optically examined and the spectra from known disease in the middle of the sample is measured and inked. In each patient, this site is considered to be representative of a positive margin since a positive margin is essentially malignant tissue extending all the way to the edge of the lumpectomy specimen.

A two-step algorithm is employed for classification of positive and negative margins: an inverse Monte Carlo model described in Palmer & Ramanujam (2006) *Appl Opt* 45:1062-1071 is employed for feature extraction (features related to breast tissue composition) from the diffuse reflectance spectra and a support vector machine classification algorithm (SVM) is used for classification based on these extracted features (see Zhu et al. (2006) *Lasers Surg Med* 38:714-724). The extracted features include absorbers and scatterers. The scattering coefficient is related to the size and density of scatterers present in the tissue (e.g., cell membranes, nuclei, structural proteins), whereas the absorption coefficient is related to the concentration of compounds present in tissue which absorb light in the visible wavelength regime (e.g., oxy- and deoxy-hemoglobin, beta carotene, and proteins).

(1) Accounting for the Effect of Lymphazurin.

One challenge that has been encountered is the effect of lymphazurin present on the surface of the lumpectomy specimens. Lymphazurin is an isosulfan blue dye, which is routinely used to aid surgeons in identification of the sentinel lymph node. This material is injected peritumorally prior to surgical resection, and is distributed throughout the axillary lymph system to a degree dependent upon the particular patient and disease state. In a majority of the cases, the dye is located on the surface of the excised specimens. The dye component of this material has significant absorption in the wavelength range being investigated and has no diagnostic value. While the Monte Carlo model employed can extract the concentration of this dye, it is currently unknown what the acceptable concentration limit for this dye is that still allows for accurate extraction of concentrations of the other diagnostically important tissue constituents. Thus, a systematic investigation of this using well-controlled liquid allowable on the surface of the tumor that does not affect the extraction of concentrations of the diagnostic absorbers is performed.

(2) Training and Cross-validation.

The tissue composition parameters extracted from optical measurements of the specimens are grouped according to pathologic analysis of the margin status of the individually interrogated sites. Then, a classification algorithm is trained on these data in order to classify future optical tissue measurements as either "positive" or "negative" for cancer. This classification algorithm is formed by using a SVM algorithm for training, which is based on machine learning theory (Palmer et al. (2006) *Appl Opt* 45:1072-1078; and Gunn (1998) "Support Vector Machines for Classification and Regression" (University of Southampton, Department of Electronics and Computer Science), available at http://homepages.cae.wisc.edu/~ece539/software/svmtoolbox/svm.pdf). The classification algorithm is trained using a linear SVM based on the most discriminatory parameters; if the data do not support this, then various non-linear SVM algorithms are investigated to determine which gives the best classification performance for the clinical data. The sensitivity, specificity, and classification accuracy of the algorithm is then estimated using the leave-one-out cross validation method (Good (2001) *Resampling Methods: A Practical Guide to Data Analysis*, Birkhäuser, Boston, Mass., United States of America). In this method, one sample is removed from the training set, and the remaining data are used to train the SVM while the removed sample is used as a test sample to assess the classification accuracy of the algorithm. This provides an unbiased estimation of the sensitivity, specificity, and accuracy of the classification algorithm.

(3) Minimum Number of Wavelengths Required to Maintain Original Sensitivity and Specificity In an effort to further streamline the data acquisition process for increased efficiency, the minimum number of wavelengths needed to maintain diagnostic accuracy are determined. Data from fewer wavelengths are retained for training and cross-validation as described above, and the sensitivity and specificity are calculated. The number of wavelengths is varied until the minimum number of wavelengths required to maintain both sensitivity and specificity to within 5% of the numbers of the original training set is determined.

Probe receiving locations 1102 of biological sample containment and illumination apparatus 100 allow parallel illumination of multiple sample sites by multiple electromagnetic radiation probes 104. The following paragraphs explain implementations of the subject matter described herein.

(A) Establishing Number of Discrete Sites that can be Sampled Simultaneously

One exemplary electromagnetic radiation probe 104 includes a circular bundle of 19 optical fibers which deliver white light to the specimen, surrounded by a ring of 4 fibers which collect light from the tissue and transmit it to a spectrograph, which disperses the broadband light into its component wavelengths and projects it onto a low-noise cooled CCD camera. This arrangement is currently used to survey a single site (approximately a few mm$^2$) on the tissue, and results in very high signal to noise (SNR; >10000) over 0.1 second integration at 500 nm, which is approximately the center wavelength of the region of interest (350-600 nm). In the proposed imaging device (see FIG. 1), the light is launched into multiple sites on the surface of the tissue by single fibers. Assuming 200 µm sized illumination fibers a total of approximately 200 fibers can be coupled to the illumination monochromator slit, thus being able to theoretically illuminate approximately 200 sites on the tissue surface. It should be noted that the light in each fiber is split into its component wavelengths before being launched into the tissue. Then, light is collected by single fibers (one or more) adjacent to each illumination fiber and transmitted to a CCD where they are imaged without spectral dispersion.

(B) Establishing Number of Collection Fibers per Illumination Fiber

The maximum number of fibers that can be imaged on a given CCD chip is determined by the size of the divergent image on the CCD chip and the size and number of pixels on the chip. Assuming 200 µm fibers with a numerical aperture of 0.22, and collimated such that the divergence is ±0.3°, then for the commercial CCD system currently used, this corresponds to a fiber image diameter of approximately 270 µm at the CCD chip. Using the specs of this CCD, and the above calculation, it is conservatively estimated that 1000 individual fibers can be resolved on a 512×512 CCD chip with 24 µm square pixel size. If 200 illumination fibers are used (the maximum allowable as determined by the light source), then this corresponds to a maximum of 5 collection fibers per illumination fiber.

Since the plan is to reduce the overall number of illumination and collection fibers at each site for parallel processing, care must be taken to ensure that it is possible to measure optical signals with reasonable SNR. A throughput analysis is performed to determine SNR for a single illumination fiber and up to 5 collection fibers for each site so that the overall SNR of each measurement site is at least 100. Based on the current SNR of the device, this should be an achievable goal. The throughput of the imaging device is further enhanced by the acquisition of a back-illuminated UV-enhanced CCD chip, which has three-fold increased quantum efficiency over the shorter wavelength range of interest than the current CCD (60% versus <20%), while exhibiting 10% higher quantum efficiency at the longer wavelengths (60% vs. 50%).

(C) Establishing the Minimum Distance Between Measurement Sites

Assuming that the imaging device has the capability to simultaneously image 200 sites, the next step is to determine the spacing between these channels on the lumpectomy specimen. One important criterion is the minimum distance between adjacent measurement sites that eliminates crosstalk between adjacent channels due to tissue scattering. Monte Carlo simulations (Wang et al. (1995) *Comput Methods Programs Biomed* 47:131-146; and Liu et al. (2003) *J Biomed Opt* 8:223-236) are performed to simulate the spatial distribution of diffusely reflected light on the tissue surface, and are carried out for the lowest absorption and highest scattering coefficient expected in normal and malignant tissues (the worst-case scenario for cross-talk). The intensity of diffusely reflected light decays exponentially from the center of the illumination fiber. The distance corresponding to the surface remitted intensity decaying to 1/e of the initial source intensity is chosen as the minimum distance allowable between adjacent measurement sites. Once the minimum separation is established then the coverage based on sampling 200 discrete sites is determined.

(D) Construction of the Device

The imaging device can be constructed as follows. The existing xenon lamp-monochromator combination in the present instrumentation is used to provide a range of wavelengths (one wavelength at a time) over the visible wavelength range. Then, a bundle of optical fibers is interfaced to the light exiting the monochromator. The individual fibers are separated at the distal end (at the sample) such that each fiber illuminates one discrete site on the specimen. The proximal end of the collection fibers are interfaced to a CCD camera. Margin imaging is performed by selecting a single wavelength with the monochromator, acquiring an image of the collection fibers on the CCD with an integration time set to achieve an SNR of at least 100, then repeating the process by scanning the monochromator over all of the desired wavelengths. This allows optical spectra to be measured from multiple sites on the face of the specimen in parallel, greatly decreasing the time required for margin analysis and creating a more efficient measurement procedure. The major modification to the existing system is replacement of the existing fiber-optic probe with an imaging bundle and replacement of the current CCD camera with a back illuminated CCD chip to accommodate as many collection fibers as possible.

(E) Testing the Feasibility of the Imaging Prototype on Lumpectomy Specimens.

After construction of the imaging device, it is tested on synthetic tissue phantoms to ascertain its performance. Liquid tissue phantoms composed of polystyrene spheres as scatterer and variable concentrations of hemoglobin as absorber are constructed with optical properties approximating those found in normal, benign, and malignant breast tissues (Palmer et al. (2006) *Appl Opt* 45:1072-1078). Diffuse reflectance "images" are acquired with the device and the resulting SNR is determined for a range of optical properties. Illumination power and integration time are adjusted until the system reaches the set benchmarks for SNR. Then, the Monte Carlo model is used to extract the absorption and scattering properties of the phantom site-by-site. Following satisfactory performance of the system on tissue phantoms, the device is then applied to lumpectomy specimens from patients undergoing BCS. A total of 5 patients are recruited to participate in this feasibility study. After resection of the specimen, the optical imaging device is used to collect an optical property map of the tissue one face at a time. The ease of use, speed, and SNR of the device are determined from this preliminary testing.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for testing a biological sample, the method comprising:
    placing a biological sample in an interior space defined by a biological sample containment and illumination apparatus having a plurality of frame members positioned with respect to each other to form a single interior volume container for holding a biological sample in an interior region defined by the container, at least one of which includes a plurality of probe receiving locations for receiving a plurality of electromagnetic radiation probes and for positioning the probes with respect to the biological sample while the biological sample is located in the interior region defined by the container to allow simultaneous illumination of plural locations of the biological sample by the probes, and further wherein at least one of the plurality of frame members is translatable with respect to another frame member such that the volume of the interior region can be altered in at least one direction and the at least one translatable frame member can be translated to vary the volume of the interior region so that the biological sample can be placed proximal to the plurality of probes;
    illuminating the biological sample through the probe receiving locations using the probes; and
    detecting electromagnetic radiation reflected from or emitted by the biological sample in response to the illumination.

2. The method of claim 1, wherein at least one of the plurality of frame members is translatable with respect to another frame member such that the volume of interior region can be altered in at least one direction.

3. The method of claim 2, comprising translating the at least one frame member to vary the volume of the interior region so that the sample can be placed proximal to the plurality of probes.

4. The method of claim 2, wherein at least two of the plurality of frame members are translatable in order to alter the volume of the interior region in at least two directions.

5. The method of claim 1, wherein the probe receiving locations are adapted to receive fiber optic probes and wherein the electromagnetic radiation probes comprise fiber optic probes.

6. The method of claim 5, wherein the probe receiving locations comprise a plurality of apertures for receiving the fiber optic probes.

7. The method of claim 6, comprising controlling advancement of each fiber optic probe in each aperture to position the fiber optic probe adjacent to the biological sample.

8. The method of claim 7, wherein controlling advancement of each fiber optic probe in each aperture comprises forming a barrier in a position adjacent proximal to the interior region to prevent the fiber optic probes from entering the interior region.

9. The method of claim 7 wherein controlling advancement of each fiber optic probe comprises coupling an adapter to one of the fiber optic probes and one of the apertures, wherein the adapter limits advancement of the one fiber optic probe in the one aperture.

10. The method of claim 9, comprising bundling the fiber optic probes together such that the adapter that limits the advancement of the one fiber optic probe limits advancement of the remaining bundled fiber optic probes in their respective apertures.

11. The method of claim 5, wherein the fiber optic probes have a sensing depth of between about 1 and 2 mm.

12. The method of claim 5, wherein each of the fiber optic probes has a geometry comprising a central core comprising a plurality of illumination fibers surrounded by at least one concentric ring comprising a plurality of collection fibers.

13. The method of claim 1, wherein the frame members form a parallelepiped structure.

14. The method of claim 13, wherein the parallelepiped structure is a rectangular parallelepiped.

15. The method of claim 1, wherein the frame members are translucent or transparent.

16. The method of claim 1, wherein the probe receiving locations are spaced from each other so as to avoid cross-talk between adjacent probes.

17. The method of claim 16, wherein each of the apertures has a diameter of about 3.7 mm and adjacent apertures have a 2 mm radial separation.

18. The method of claim 1 wherein illuminating the biological sample includes illuminating plural locations on the biological sample in parallel through different probe receiving locations.

19. A system for imaging a sample, the system comprising:
a biological sample containment and illumination apparatus for holding a biological sample for illumination by a plurality of electromagnetic radiation probes, the biological containment and illumination apparatus comprising a plurality of frame members positioned with respect to each other to form a single interior volume container for holding a biological sample in an interior region defined by the container, wherein at least one of the plurality of frame members includes a plurality of probe receiving locations for receiving a plurality of electromagnetic radiation probes and for positioning the probes with respect to the biological sample while the biological sample is located in the interior region defined by the container to allow simultaneous illumination of plural locations of the biological sample by the probes, and further wherein at least one of the plurality of frame members is translatable with respect to another frame member such that the volume of the interior region can be altered in at least one direction and the at least one translatable frame member can be translated to vary the volume of the interior region so that the biological sample can be placed proximal to the plurality of probes;
a plurality of electromagnetic radiation probes for illuminating the plural locations of the biological sample via the probe receiving locations with electromagnetic radiation generated by an electromagnetic radiation source and for detecting electromagnetic radiation reflected from or emitted by the biological sample via the probe receiving locations;
a detector coupled to the probes for receiving electromagnetic radiation signals indicative of the electromagnetic radiation detected by the probes and for converting the electromagnetic radiation signals to electrical signals; and
a processor coupled to the detector for receiving the electrical signals and for determining, based on the electrical signals an indication of a physical property of the biological sample.

20. The system of claim 19, wherein at least one of the plurality of frame members is translatable with respect to another frame member such that the volume of the interior region can be altered in at least one direction.

21. The system of claim 20, wherein the at least one translatable frame member can be translated to vary the volume of the interior region so that the biological sample can be placed proximal to the plurality of probes.

22. The system of claim 19, wherein at least two of the plurality of frame members are translatable in order to alter the volume of the interior region in at least two directions.

23. The system of claim 19, wherein the probe receiving locations are adapted to receive fiber optic probes and wherein the electromagnetic radiation probes comprise fiber optic probes.

24. The system of claim 23, wherein the probe receiving locations comprise a plurality of apertures for receiving the fiber optic probes.

25. The system of claim 24, comprising means for controlling advancement of each fiber optic probe in each aperture to position the fiber optic probe adjacent to the biological sample.

26. The system of claim 25, wherein the means for controlling advancement of each fiber optic probe in each aperture comprises a barrier located in a position proximal to the interior region to prevent the fiber optic probes from entering the interior region.

27. The system of claim 25, wherein the means for controlling advancement comprises an adapter couplable to one of the fiber optic probes and one of the apertures to limit advancement of the one probe in the one aperture.

28. The system of claim 27, wherein the plurality of fiber optic probes are fixedly attached to each other such that the adapter that limits advancement of the one fiber optic probe limits advancement of the remaining bundled fiber optic probe in their respective apertures.

29. The system of claim 23, wherein the fiber optic probes have a sensing depth of between about 1 and 2 mm.

30. The system of claim 23, wherein the fiber optic probes have a geometry comprising a central core comprising a plurality of illumination fibers surrounded by at least one concentric ring comprising a plurality of collection fibers.

31. The system of claim 19, wherein the frame members form a parallelepiped structure.

32. The system of claim 31, wherein the parallelepiped structure is a rectangular parallelepiped.

33. The system of claim 19, wherein the frame members are translucent or transparent.

34. The system of claim 19, wherein the probe receiving locations are spaced from each other so as to avoid cross-talk between adjacent probes.

35. The system of claim 34, wherein each of the apertures has a diameter of about 3.7 mm and adjacent apertures have a 2 mm radial separation.

36. The system of claim 19, wherein the biological sample comprises a turbid medium having a concentration of one or more fluorophores and wherein the processor is adapted to determine an indication of the concentration of the one or more fluorophores based on the detected electromagnetic radiation.

37. The system of claim 36, wherein the turbid medium is a biological tissue sample.

38. The system of claim 37, wherein the indication of the physical property of the biological tissue sample is indicative of the biological tissue sample comprising normal cells, pre-neoplastic cells, neoplastic cells, or combinations thereof.

39. The system of claim 36, wherein the turbid medium comprises one or more absorbers and one or more scatterers and wherein the processor is adapted to determine an indication of the concentration of the absorber and the scattering coefficient.

40. The system of claim 19, wherein the electromagnetic radiation probes are adapted to illuminate plural locations of the biological sample in parallel via different probe receiving locations.

* * * * *